(12) United States Patent
Kelsey et al.

(10) Patent No.: US 6,245,879 B1
(45) Date of Patent: Jun. 12, 2001

(54) PURIFICATION OF 1,3-PROPANEDIOL IN CARBONYL-CONTAINING STREAM

(75) Inventors: Donald Ross Kelsey, Fulshear; Betty Marrou Scardino, Katy, both of TX (US); Steven Charles Zronek, Martinez, CA (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/239,900

(22) Filed: Jan. 29, 1999

(51) Int. Cl.$^7$ ............................. C08G 63/78; C08F 2/00
(52) U.S. Cl. ............... 528/275; 528/282; 528/308.6; 524/779; 526/65; 526/66; 526/67; 526/68; 526/71
(58) Field of Search ............... 528/275, 282, 528/308.6; 524/779; 526/65, 66, 67, 68, 71

(56) References Cited

U.S. PATENT DOCUMENTS

| | | | |
|---|---|---|---|
| 4,105,701 | 8/1978 | Larkin | 260/650 |
| 5,334,778 | 8/1994 | Haas et al. | 568/862 |
| 5,459,229 | 10/1995 | Kelsey et al. | |
| 5,527,973 | 6/1996 | Kelsey | 568/862 |

FOREIGN PATENT DOCUMENTS

WO 98/49216    5/1998   (WO) .

OTHER PUBLICATIONS

Database WPI—Section Ch, Week 199626—Derwent Publication, Ltd., Class E17, AN 1996–25 79 78 RU 2,046, 788—Oct. 27, 1995 (Abstract), Dec. 5, 2000.
International Search Report May 12,2000.
Morton International VenPure® Technical Manual, pp. 3, 4, 5, 17 (no date).

*Primary Examiner*—Samuel A. Acquah

(57) ABSTRACT

A process for preparing polytrimethylene terephthalate in which a carbonyl-containing 1,3-propanediol stream is purified for reuse of the 1,3-propanediol. The process involves reacting, under condensation polymerization conditions, terephthalic acid and a molar excess of 1,3-propanediol, with vacuum distillation and condensation of a major portion of the unreacted 1,3-propanediol. To this condensed stream is added a sufficient amount of base to raise the pH to a value greater than 7, and from this base-containing condensate the 1,3-propanediol is distilled and recycled to the polymerization reaction.

17 Claims, No Drawings

PURIFICATION OF 1,3-PROPANEDIOL IN CARBONYL-CONTAINING STREAM

BACKGROUND OF THE INVENTION

This invention relates to the purification of a carbonyl-containing 1,3-propanediol composition. In a specific aspect, the invention relates to treatment of a 1,3-propanediol-containing stream from the manufacture of polytrimethylene terephthalate so as to permit recycle of the 1,3-propanediol to the polymerization process.

Polytrimethylene terephthalate is a polyester useful in making fibers for carpets and textiles. In the preparation of polytrimethylene terephthalate by the esterification/condensation polymerization of 1,3-propanediol and terephthalic acid, the 1,3-propanediol is initially present in the esterification reaction mixture in a molar excess with respect to the acid. In order to achieve high polymer molecular weight, excess 1,3-propanediol is removed under vacuum and condensed as the polycondensation reaction proceeds. This condensed 1,3-propanediol stream typically also contains carbonyl-containing by-products of the polymerization process.

Although it would be desirable to recycle this excess 1,3-propanediol to the polymerization process, the addition of the by-products along with the 1,3-propanediol could result in the accumulation of carbonyl-containing byproducts in the system and interfere with the production of high-quality polyester.

It is known to purify such byproduct streams by adding a substantial amount of water, acidifying the solution, and then distilling the 1,3-propanediol under basic conditions. It would be desirable to recover purified 1,3-propanediol from the byproduct stream without the necessity of adding large quantities of water to the system.

It is therefore an object of the invention to provide a process for preparing polytrimethylene terephthalate in which relatively pure 1,3-propanediol is recovered from the distillate stream and recycled to the polymerization process.

BRIEF SUMMARY OF THE INVENTION

According to the invention, polytrimethylene terephthalate is prepared in a process comprising the steps of:

(a) contacting, in a polymerization reaction mixture at a temperature within the range of about 200 to about 300° C. under less than atmospheric pressure, terephthalic acid (or ester thereof) and a molar excess of 1,3-propanediol, for a time sufficient to produce a reaction product mixture comprising polytrimethylene terephthalate and a distillate comprising unreacted 1,3-propanediol, by-product carbonyl compounds and a minor amount of water;

(b) adding a sufficient amount of a base to impart to the distillate a pH higher than 7;

(c) heating the base-containing distillate to a temperature sufficient to distill a major portion of the 1,3-propanediol from the mixed condensate; and (d) passing at least a portion of the distilled 1,3-propanediol to the polymerization reaction mixture as a recycle stream.

DETAILED DESCRIPTION OF THE INVENTION

The invention process involves adding a base to a carbonyl-containing 1,3-propanediol composition. As used herein, "carbonyl" refers to a compound, whether containing the C=O group or not, detected by a method in which total carbonyls are determined by conversion to 2,4-nitrophenylhydrazone derivatives and measured calorimetrically, such as ASTM E411-70. The source of such carbonyl species can be acetals, aldehydes or ketones.

The carbonyl-containing 1,3-propanediol composition is a distillate stream from the preparation of polytrimethylene terephthalate. As used herein, "1,3-propanediol-based polyester" refers to a polyester prepared by reacting at least one diol with at least one aromatic diacid (or alkyl ester thereof) in which at least 80 mole percent of the diol is 1,3-propanediol. "Polytrimethylene terephthalate" refers to such a polyester in which at least 80 mole percent of the diacid is terephthalic acid (or an alkyl ester thereof). Other diols may include, for example, ethylene glycol, diethylene glycol, 1,4-cyclohexanone dimethanol, bis(3-hydroxypropyl)ether and 1,4-butanediol, and other diacids may include, for example, isophthalic acid and 2,6-naphthalene dicarboxylic acid. The condensation polymerization of polytrimethylene terephthalate usually generates as much as about 4 mole percent of bis(3-hydroxypropyl)ether which, in effect, becomes a comonomer and is incorporated into the polyester chain.

Polytrimethylene terephthalate is prepared by the polycondensation reaction of the 1,3-propanediol with terephthalic acid (or an alkyl ester thereof) under vacuum and at a temperature within the range of about 200 to about 300° C. The diol(s) are added to the polymerization reaction mixture in a molar excess of 5 to 50% or more with respect to the acid. As the polycondensation reaction proceeds, the excess diol is removed under vacuum and condensed. The condensed stream typically contains, in addition to about 70 wt % or more diol(s), polymerization byproducts such as allyl alcohol, acrolein and other carbonyl compounds, acetals, alcohols, glycol ethers, diacids, polyester oligomers and adducts, and about 1–20 wt % water. Additional 1,3-propanediol can be added if needed to adjust the water concentration to this range. The carbonyl content (as C=O) of the distillate stream can typically range from 500 to 2500 ppm, depending upon the purity of the starting 1,3-propanediol and the polymerization reaction conditions. The pH of the stream is typically within the range of about 3 to about 6. The diol product of the invention treatment process preferably contains less than about 300 ppm carbonyl, most preferably less than about 200 ppm, qualifying it for use as a recycle stream in high-quality polyester manufacture.

A base is added to the 1,3-propanediol-containing composition in an amount sufficient to raise the pH thereof to a value greater than 7, preferably about 7.5 to about 14, most preferably within the range of about 8 to about 10. If desired, the base can be added in increments over the course of the purification process. The amount of base added is nominally the amount needed to neutralize acidic species present in the condensed stream plus any amount needed to reach the target pH. However, additional base may be needed, particularly if the stream contains soluble or suspended polyester adducts or oligomers, since reaction of the base with these oligomers or other impurities may consume base during the purification process. If the stream contains solid polymerization by-products, it is preferable to remove such solids by, for example, filtration prior to addition of the base to the liquid mixture.

Suitable bases for the purification treatment are typically inorganic bases such as the alkali and alkaline earth hydroxides, carbonates and bicarbonates. Preferred bases are sodium and potassium hydroxides. Organic bases such as amines are to be avoided.

The base-containing condensed stream is optionally further treated with a borohydride represented by the formula $MBH_xY_y$, in which M is an alkali metal cation or a tetraalkylammonium cation, Y is a ligand, x is at least 1, and x+y=4, with x=4 and y=0 most preferred. Examples of such borohydrides include the metal tetrahydridoborates such as lithium borohydride, potassium borohydride, sodium borohydride and rubidium borohydride; metal organoborohydrides such as lithium trimethylborohydride, lithium triethylborohydride, lithium thexylborohydride, potassium tri-iso-amylborohydride, potassium tri-sec-butylborohydride, potassium triethylborohydride, potassium triphenylborohydride, sodium triacetoxyborohydride, sodium tri-iso-amylborohydride, sodium tri-sec-butylborohydride, sodium triethylborohydride, sodium trimethyloxyborohydride, and sodium triphenylborohydride; tetraalkylammonium borohydrides such as tetramethylammonium borohydride, tetraethylammonium borohydride and tetrabutylammonium borohydride. Potassium borohydride, sodium borohydride and tetraalkylammonium borohydrides are preferred. If desired, the borohydride can be used in supported form on basic alumina, silica gel and the like.

The amount of borohydride added to the condensed stream will generally be that amount which provides about 0.2 to about 20 gram atoms of hydrogen atoms per mole of carbonyls, as defined herein, in the stream. In the case of the preferred potassium, sodium and tetraalkylammonium borohydrides, the amount will generally range from about 0.05 to about 5 moles, preferably about 0.1 to about 1 mole, of borohydride per mole of carbonyl present in the stream.

Because borohydrides are generally unstable under acidic conditions, the borohydride is preferably added after at least a portion of the base has been added to the condensed stream. If desired, a small quantity of water can be added to the condensed stream for a total water content up to of 20 wt % to facilitate dissolution of the more polar borohydrides such as sodium and potassium borohydrides.

Following the addition of borohydride and prior to distillation, the condensed stream may optionally be heated and maintained at a temperature within the range of about 40 to about 100° C. for a few minutes to several hours, preferably a time within the range of about 15 minutes to about 24 hours Alternatively, the condensed stream may be heated directly to the temperature at which distillation of the 1,3-propanediol will be carried out.

Distillation is typically carried out by boiling off water, if present, and other low-boiling components at atmospheric or reduced pressure, and then distilling off 1,3-propanediol, preferably at reduced pressure less than about 200 mbar and a temperature within the range of about 60 to about 160° C. to avoid excessive heating of the 1,3-propanediol.

The invention can be practiced as a series of batch, semi-batch, semi-continuous or continuous processes.

The purified 1,3-propanediol can be used, for example, to prepare condensation polymers and copolymers. The purified 1,3-propanediol is particularly useful as a monomer recycle stream for addition to a fresh 1,3-propanediol feed to polytrimethylene terephthalate manufacture.

EXAMPLE 1

Purification of 1,3-Propanediol-Containing Stream

A flask with magnetic stir bar was charged with 250 g of a vacuum distillate recovered from preparation of polytrimethylene terephthalate having (after filtration to remove a minor amount of solids) about 15% water, a pH of about 3.6, 1190 ppm carbonyls (as C=O), 1370 ppm acrolein by GC, about 5% allyl alcohol, minor amounts of other glycols, about 0.7% terephthalic acid (after hydrolysis of any soluble terephthalic esters), about 10–15 ppm iron and about 80% 1,3-propanediol. The pH of this solution was adjusted to 8.96 by addition of about 10 ml 1N solution of sodium hydroxide. The solution was heated in an oil bath under reduced pressure and distilled through a 30 cm Vigreaux distillation column and chilled condenser to provide a forecut (69 g) and a major cut (141 g, b.p. 127° C.), the latter collected at an oil bath temperature of about 150° C. and about 35–65 mbar. Carbonyl analyses of the fractions—forecut, major cut and bottoms (41 g)—are shown in Table 1.

EXAMPLE 2

Purification of 1,3-Propanediol-Containing Stream

The procedure of Example 1 was repeated, except that, after adjustment of the pH, the mixture was allowed to stand at room temperature for about 67 hours, after which the pH had dropped to about 7.9. Additional sodium hydroxide was added to bring the pH to about 8.7 and the mixture was distilled. A water-rich cut was taken and then the forecut and major cuts were collected. Carbonyl analyses are shown in Table 1.

EXAMPLE 3

Purification of 1,3-Propanediol-Containing Stream

The procedure of Example 2 was repeated (without pH readjustment), except that the 1,3-propanediol stream was a vacuum distillate recovered from polytrimethylene terephthalate preparation having a pH (after filtration to remove solids) of 3.9, 773 ppm carbonyl, less than 10 ppm acrolein, 440 ppm allyl alcohol, minor amounts of other glycols, about 0.5% terephthalic acid (after hydrolysis), at least about 94% 1,3-propanediol, and less than about 1% water. This distillate had been stored for several months at ambient conditions. Carbonyl analyses are shown in Table 1.

EXAMPLE 4

Purification of 1,3-Propanediol-Containing Stream

The procedure of Example 1 was repeated, except that the stream was diluted with about 175 g deionized water to make a 50% 1,3-propanediol solution prior to being adjusted to 9.1 pH with NaOH. A water cut was collected before the forecut. Carbonyl analyses are shown in Table 1. The example shows that dilution with water does not substantially improve the purification in that the carbonyl content of the major fraction obtained is similar to that obtained in Example 1.

TABLE 1

| | Ex. 1 | | Ex. 2 | | Ex. 3 | | Ex. 4 | | Ex. 5 | | Ex. 6 | | Ex. 7 | |
|---|---|---|---|---|---|---|---|---|---|---|---|---|---|---|
| | wt. | C=O | wt. | C=O | wt. | C=O | wt. | C=O | wt. | C=O | wt. | C=O | wt. | C=O |
| Initial | | 1190 | | 1190 | | 773 | | 1190 | | 773 | | 773 | | 1190 |
| Water Cut | | | 54 | 1690 | | | 212 | 352 | 219 | 23 | | | | |
| Forecut | 69 | 1650 | 30 | 1240 | 40 | 320 | 37 | 685 | 34 | 226 | 60 | 453 | 64 | 1170 |
| Major Cut | 141 | 62 | 103 | 71 | 140 | 83 | 128 | 79 | 162 | 79 | 150 | 134 | 134 | 226 |
| Bottoms | 41 | 1160 | 35 | 1530 | 54 | 3000 | 50 | 1250 | 38 | 3070 | 40 | 2700 | 52 | 4300 |

| | Ex. 8 | | Ex. 9 | | Ex. 10 | | Ex. 11 | | Ex. 12 | | Ex. 13 | |
|---|---|---|---|---|---|---|---|---|---|---|---|---|
| | wt. | C=O | wt. | C=O | wt. | C=O | wt. | C=O | wt. | C=O | wt. | C=O |
| Initial | | 773 | | 773 | | 773 | | 1190 | | 1190 | | 773 |
| Water Cut | 229 | 20 | | | | | | | 52 | 980 | | |
| Forecut | 55 | 258 | 54 | 191 | 85 | 86 | 101 | 641 | 31 | 142 | 44 | 306 |
| Major Cut | 170 | 139 | 131 | 52 | 100 | 70 | 129 | 42 | 128 | 50 | 152 | 59 |
| Bottoms | 37 | 3000 | 36 | 3310 | 55 | 1820 | 34 | 1420 | 39 | 1870 | 54 | 2400 |

Note: weight of distillation cuts to nearest gram; carbonyls are ppm (wt) as C=O and rounded to two or three significant figures.

EXAMPLE 5

Purification of 1,3-Propanediol-Containing Stream

The procedure of Example 4 was repeated using the 1,3-propanediol stream described in Example 3 and 250 g water to make the 50% solution. Carbonyl analyses are shown in Table 1.

EXAMPLE 6

Recovery of 1.3-Propanediol by Distillation Alone

This comparative experiment was performed by distilling the distillate stream described in Example 3 by the procedure described in Example 1 but without treatment with a base. The major cut of 1,3-propanediol showed significantly higher levels of carbonyls than those of Examples 1–5. Carbonyl analyses are shown in Table 1.

EXAMPLE 7

Recovery of 1,3-Propanediol by Distillation Alone

This comparative experiment was performed by distilling the distillate stream described in Example 1 by the method of Example 1, but without treatment with a base. The major cut of PDO showed significantly higher levels of carbonyls than those of Examples 1–5.

EXAMPLE 8

Recover of 1,3-Propanediol by Distillation of a Dilute Stream

This comparative experiment was performed as described in Example 6, except that the 1,3-propanediol stream was diluted with deionized water to make a solution of about 50% 1,3-propanediol, and this aqueous solution was adjusted to a pH of about 3 by addition of a small amount of p-toluenesulfonic acid. The solution was heated at 45–55° C. for about one hour, followed by distillation. The major cut contained a higher level of carbonyls than obtained in Example 3.

EXAMPLE 9

Purification of 1,3-Propanediol-Containing Stream with Added Borohydride

A flask was charged with 250 g of the 1,3-propanediol stream described in Example 3 and the pH was adjusted to 9 by addition of 1N NaOH. After addition of tetraethylammonium borohydride (1g, 6.9 mmol), the reaction mixture was degassed with nitrogen and heated to 75° C. for 50 minutes under nitrogen purge. The solution was then distilled as in the previous examples. The results are shown in Table 1.

EXAMPLE 10

Purification of 1,3-Propanediol-Containing Stream with Added Borohydride

The procedure of Example 9 was repeated, except that 212.5 g of the 1,3-propanediol stream was mixed with 37.59 g deionized water to give a solution of about 85% 1,3-propanediol in water containing about 1.9 mmol carbonyls. After adjustment of the pH to 9.5 with 1N NaOH, 0.23 g (6.1 mmol) sodium borohydride was added, the reaction mixture was heated to 70° C. for about one hour, and the mixture was distilled. Carbonyl analyses are shown in Table 1.

EXAMPLE 11

Purification of 1.3-Propanediol-Containing Stream with Added Borohydride

The procedure of Example 9 was repeated, except that 250 g of the 1,3-propanediol stream described in Example 1 was used (about 10.6 mmol carbonyls), the adjusted pH was 9.2, and 0.40 g (10.6 mmol) sodium borohydride was added. Carbonyl analyses are shown in Table 1.

EXAMPLE 12

Purification of 1.3-Propanediol-Containing Stream with Added Borohydride

The procedure of Example 11 was repeated, except that the pH was adjusted to 8.6 and 0.8 g (21 mmol) sodium borohydride was added. Carbonyl analyses are shown in Table 1.

EXAMPLE 13

Purification of 1,3-Propanediol-Containing Stream with Added Borohydride

The procedure of Example 10 was repeated, except that there was no adjustment of pH prior to addition of 1 g (6.9 mmoles) borohydride. The reaction mixture turned black while it was being degassed. After heating for an hour at 75° C., the black mixture was distilled. Although the major cut had low carbonyls, the formation of the black color suggests decomposition of the borohydride or other unwanted side reaction.

As can be seen from the results of Table 1, the use of base and borohydride gave similar or somewhat lower concentrations of carbonyls in the major cuts compared to the use of base alone. In the case of the fresher distillate, the carbonyl levels measured in the forecuts and bottoms were less with base/borohydride than for comparable runs using base alone, which would be an advantage for recycle of one or both of these fractions.

Doubling the amount of borohydride (Example 12) did not substantially reduce the total amount of carbonyls (compare Example 11), which demonstrates that a large proportion of the "carbonyls" in the 1,3-propanediol are not subject to reduction by hydrides, such as would be the case for acetals. Thus, the base treatment with distillation is an effective procedure even in the absence of the borohydride.

about 1 mbar. After 3 hours, the reaction mixture was cooled and the polymer was isolated. Results are shown in Table 2.

As can be seen from the results, the purified 1,3-propanediol (from Examples 1 and 11) produced less acrolein in the aqueous distillate, less acrolein and total carbonyls in the 1,3-propanediol distillate, and higher molecular weight than unpurified commercial-grade 1,3-propanediol.

TABLE 2

| PDO | Aqueous Distillate | | | PDO Distillate | | | |
|---|---|---|---|---|---|---|---|
| | Carbonyls[a] (ppm) | Acrolein (ppm) | Allyl Alcohol (%) | Acrolein (ppm) | Carbonyls[a] (ppm) | IV[b] | YI[c] |
| Ex. 1 | 62 | 180 | 0.24 | 1210 | 940 | 1.14 | 3.5* |
| Ex. 11 | 42 | 780 | 0.44 | 2160 | 2770 | 1.24 | 1.3* |
| Commerc. | 300 | 2700 | 0.72 | 2570 | 3840 | 1.09 | 29.9 |

[a]As C=O
[b]IV is intrinsic viscosity in hexafluoroisopropanol at 25° C.
[c]YI is yellowness index as measured by ASTM D-1925.
*Grinding these samples produced some graying which could result in lower YI

EXAMPLE 14

Polymerization of Treated 1,3-Propanediol

The purified 1,3-propanediol (major cuts) from Examples 1 and 11 was used to prepare polytrimethylene terephthalate oligomer. A 600 ml stainless steel pressure reactor fitted with a distillation column, condenser and collection vessel was charged with 66.6 g of 1,3-propanediol (0.88 mole) and 103.9 g terephthalic acid (0.63 mole). The reactor was pressurized to 50–80 psi with nitrogen, the pressure was released five times to degas, then the vessel was repressurized to 20 psi and heated to 250° C. For the first two hours, the pressure was maintained near 50 psi and was then lowered in 10 psi increments each hour thereafter. After a total of about 6 hours, any remaining pressure was released, and the aqueous distillate was collected, weighed and analyzed by GC. The molten oligomer was poured into a pan and cooled. The results are shown in Table 2.

The oligomer (140 g) and 0.09 g titanium butoxide catalyst were charged to a 500-ml 3-neck flask. The flask was degassed with nitrogen, evacuated to about 200 mbar with a small nitrogen sweep, heated in an oil bath to 260° C., and stirred at about 20 rpm. The pressure was reduced to

We claim:

1. A process for preparing a 1,3-propanediol-based polyester comprising:
   (a) contacting, in a polymerization reaction mixture at a temperature within the range of about 200 to about 280° C. under less than atmospheric pressure, terephthalic acid and a molar excess of 1,3-propanediol, to produce a reaction product mixture comprising polytrimethylene terephthalate and a distillate comprising excess 1,3-propanediol, by-product carbonyl compounds and less than 20 wt % water;
   (b) adding a sufficient amount of a base to impart to the distillate a pH higher than 7, said addition of base achieved without raising the water content of the base-containing distillate above 20 wt %;
   (c) heating the base-containing distillate to a temperature sufficient to distill a major portion of the 1,3-propanediol therefrom; and
   (d) passing at least a portion of said distilled 1,3-propanediol to the polymerization reaction mixture as a recycle stream.

2. The process of claim 1 in which the pH of step (c) is within the range of about 8 to about 10.

3. The process of claim 1 in which the base is selected from the group consisting of sodium hydroxide and potassium hydroxide.

4. The process of claim 1 which further comprises removing any solids from the distillate prior to addition of the base.

5. The process of claim 1 in which the distillate contains at least about 500 ppm carbonyl compounds, as C=O.

6. The process of claim 1 in which the distillation of step (c) is carried out under less than atmospheric pressure and at a temperature within the range of about 60 to about 160° C.

7. The process of claim 1 in which the base-containing distillate is maintained at a temperature less than that sufficient for distillation of the 1,3-propanediol therefrom for a time of at least 1 hour prior to such distillation.

8. The process of claim 1 in which the base containing distilliate contains less than about 10 wt % water.

9. The process of claim 1 in which the base is sodium hydroxide.

10. The process of claim 1 which further comprises adding a borohydride of the formula $MBH_xY_y$, in which M is an alkali metal or tetraalkylammonium cation, y is a ligand, x is at least 1 and x+y=4, to the base-containing distillate prior to distillation of 1,3-propanediol therefrom.

11. The process of claim 10 in which the borohydride is selected from the group consisting of potassium borohydride, sodium borohydride and tetraalkylammonium borohydrides.

12. The process of claim 10 in which the borohydride is tetraethylammonium borohydride.

13. The process of claim 10 in which the borohydride is sodium borohydride.

14. The process of claim 10 in which the borohydride is added in an amount within the range of about 0.05 to about 5 moles per mole of carbonyl.

15. The process of claim 10 in which the borohydride is added in an amount within the range of about 0.1 to about 1 mole per mole of carbonyl.

16. The process of claim 1 in which the 1,3-propanediol-based polyester is polytrimethylene terephthalate.

17. The process of claim 1 in which step (a) comprises adding 1,3-propanediol to the distillate to reduce the water content thereof to less than 20 wt %.

* * * * *